United States Patent
Shams et al.

(10) Patent No.: US 7,512,496 B2
(45) Date of Patent: Mar. 31, 2009

(54) APPARATUS, METHOD, AND COMPUTER PROGRAM PRODUCT FOR DETERMINING CONFIDENCE MEASURES AND COMBINED CONFIDENCE MEASURES FOR ASSESSING THE QUALITY OF MICROARRAYS

(76) Inventors: Soheil Shams, 1706 Clark La. "B", Redondo Beach, CA (US) 90278; Anton Petrov, 1001 Figueroa Ter. #307, Los Angeles, CA (US) 90012

( * ) Notice: Subject to any disclaimer, the term of this patent is extended or adjusted under 35 U.S.C. 154(b) by 0 days.

(21) Appl. No.: 10/256,101

(22) Filed: Sep. 25, 2002

(65) Prior Publication Data

US 2004/0059520 A1    Mar. 25, 2004

(51) Int. Cl.
G01N 33/48    (2006.01)
(52) U.S. Cl. .......................................... 702/19; 702/20
(58) Field of Classification Search ................. 702/19; 435/287.2
See application file for complete search history.

(56) References Cited

U.S. PATENT DOCUMENTS

| | | | |
|---|---|---|---|
| 4,550,084 A | 10/1985 | Nelson et al. | 436/45 |
| 4,641,528 A | 2/1987 | Clayland, Jr. et al. | 73/597 |
| 5,121,320 A | 6/1992 | Aoki et al. | 364/413.01 |
| 5,134,662 A | 7/1992 | Bacus et al. | 382/6 |
| 5,202,932 A | 4/1993 | Cambier et al. | 382/8 |
| 5,273,632 A | 12/1993 | Stockham et al. | 204/180.1 |
| 5,389,792 A | 2/1995 | DiMarzio et al. | 250/370.06 |
| 5,417,923 A | 5/1995 | Bojanic et al. | 422/101 |
| 5,541,064 A | 7/1996 | Bacus et al. | 435/6 |
| 5,552,270 A | 9/1996 | Khrapko et al. | 435/6 |
| 5,560,811 A | 10/1996 | Briggs et al. | 204/451 |
| 5,580,728 A | 12/1996 | Perlin | 435/6 |
| 5,581,631 A | 12/1996 | Ortyn et al. | 382/128 |
| 5,583,973 A | 12/1996 | DeLisi et al. | 395/120 |
| 5,680,514 A | 10/1997 | Shams | 395/22 |
| 5,695,937 A | 12/1997 | Kinzler et al. | 435/6 |
| 5,720,928 A | 2/1998 | Schwartz | 422/186 |
| 5,732,277 A | 3/1998 | Kodosky et al. | 395/800 |
| 5,757,954 A | 5/1998 | Kuan et al. | 382/133 |
| 5,773,218 A | 6/1998 | Gallatin et al. | 435/6 |
| 5,777,888 A | 7/1998 | Rine et al. | 364/496 |
| 5,785,658 A | 7/1998 | Benaron et al. | 600/473 |
| 5,811,517 A | 9/1998 | Gallatin et al. | 530/350 |

(Continued)

FOREIGN PATENT DOCUMENTS

WO    WO 01/16860    3/2001

(Continued)

OTHER PUBLICATIONS

BIO001—M. Burl, "Recognition of Visual Object Classes", *Jet Propulsion Laboratory*, V-0105, Mar. 30, 1996, 12 pages.

(Continued)

*Primary Examiner*—Cheyne D Ly
(74) *Attorney, Agent, or Firm*—Tope-McKay & Associates

(57) ABSTRACT

An apparatus, method, and computer program product are provided for determining a confidence measure for the output of a process for assessing proteomic and genomic information samples. Typically, data is received as the results from a microarry experiment. The confidence measure is intended to determine whether the results of the experiment have been degraded due to experimental error. Several criteria are used by which quality is determined. The criteria are preferably combined into a combined quality measure in order to account for several possible sources of error.

18 Claims, 10 Drawing Sheets

U.S. PATENT DOCUMENTS

| | | | | |
|---|---|---|---|---|
| 5,837,475 | A | 11/1998 | Dorsel et al. | 435/7.1 |
| 5,851,769 | A | 12/1998 | Gray et al. | 435/6 |
| 5,853,979 | A | 12/1998 | Green et al. | 435/5 |
| 5,865,975 | A | 2/1999 | Bishop | 204/618 |
| 5,869,262 | A | 2/1999 | Gallatin et al. | 435/7.1 |
| 5,876,933 | A | 3/1999 | Perlin | 435/6 |
| 5,880,268 | A | 3/1999 | Gallatin et al. | 530/387.3 |
| 5,887,074 | A | 3/1999 | Lai et al. | 382/128 |
| 5,916,747 | A | 6/1999 | Gilchrist et al. | 435/6 |
| 5,945,284 | A | 8/1999 | Livak et al. | 435/6 |
| 5,945,679 | A | 8/1999 | Dorsel et al. | 250/458.1 |
| 5,970,164 | A | 10/1999 | Bamberger et al. | 382/128 |
| 5,980,096 | A | 11/1999 | Thalhammer-Reyero | 364/578 |
| 5,981,190 | A | 11/1999 | Israel | 435/6 |
| 5,989,835 | A | 11/1999 | Dunlay et al. | 435/7.2 |
| 6,040,176 | A | 3/2000 | Gallatin et al. | 435/326 |
| 6,054,270 | A | 4/2000 | Southern | 435/6 |
| 6,057,101 | A | 5/2000 | Nandabalan et al. | 435/6 |
| 6,083,693 | A | 7/2000 | Nandabalan et al. | 435/6 |
| 6,100,383 | A | 8/2000 | Gallatin et al. | 530/387.3 |
| 6,103,479 | A | 8/2000 | Taylor | 435/7.2 |
| 6,127,129 | A | 10/2000 | Corn et al. | 435/6 |
| 6,150,179 | A | 11/2000 | Went | 436/173 |
| 6,185,561 | B1 | 2/2001 | Balaban et al. | 707/6 |
| 6,203,987 | B1 | 3/2001 | Friend et al. | 435/6 |
| 6,207,958 | B1 | 3/2001 | Giakos | 250/385.1 |
| 6,222,093 | B1 | 4/2001 | Marton et al. | 800/3 |
| 6,223,186 | B1 | 4/2001 | Rigault et al. | 707/104 |
| 6,226,542 | B1 | 5/2001 | Reisfeld | 600/407 |
| 6,245,517 | B1 | 6/2001 | Chen et al. | 435/6 |
| 6,251,601 | B1 | 6/2001 | Bao et al. | 435/6 |
| 6,263,092 | B1 | 7/2001 | Roehrig et al. | 382/128 |
| 6,263,287 | B1 | 7/2001 | Zheng et al. | 702/20 |
| 6,301,378 | B1 | 10/2001 | Karssemeijer et al. | 382/132 |
| 6,303,301 | B1 | 10/2001 | Mack | 435/6 |
| 6,308,170 | B1 | 10/2001 | Balaban | 707/3 |
| 6,341,256 | B1 | 1/2002 | Deem et al. | 702/19 |
| 6,345,115 | B1 | 2/2002 | Ramm et al. | 382/133 |
| 6,349,144 | B1 | 2/2002 | Shams | 382/129 |
| 6,351,712 | B1 | 2/2002 | Stoughton et al. | 702/19 |
| 6,362,004 | B1 | 3/2002 | Noblett | 436/43 |
| 6,362,832 | B1 | 3/2002 | Stephan et al. | 345/629 |
| 6,381,058 | B2 | 4/2002 | Ramm et al. | 359/242 |
| 6,389,428 | B1 | 5/2002 | Rigault et al. | 707/104.1 |
| 6,441,973 | B1 | 8/2002 | Ramm et al. | 359/778 |
| 6,453,241 | B1 | 9/2002 | Bassett, Jr. et al. | 702/19 |
| 6,462,187 | B1 | 10/2002 | Bandaru | 536/23.2 |
| 6,470,277 | B1 | 10/2002 | Chin et al. | 702/19 |
| 6,475,736 | B1 | 11/2002 | Stanton, Jr. | 435/6 |
| 6,498,690 | B2 | 12/2002 | Ramm et al. | 359/778 |
| 6,498,863 | B1 | 12/2002 | Gaidoukevitch et al. | 382/173 |
| 6,537,749 | B2 | 3/2003 | Kuimelis et al. | 435/6 |
| 6,544,790 | B1 | 4/2003 | Sabatini | 435/455 |
| 6,553,317 | B1 | 4/2003 | Lincoln et al. | 702/20 |
| 6,577,956 | B1 | 6/2003 | Shams | 702/19 |
| 6,591,196 | B1 | 7/2003 | Yakhini et al. | 702/28 |
| 6,632,600 | B1 | 10/2003 | Short | 435/4 |
| 6,633,659 | B1 | 10/2003 | Zhou | 382/129 |
| 6,673,549 | B1 | 1/2004 | Furness et al. | 435/6 |
| 6,674,882 | B1 | 1/2004 | Shams | 382/129 |
| 6,683,455 | B2 | 1/2004 | Ebbels et al. | 324/309 |
| 6,690,399 | B1 | 2/2004 | Carlson et al. | 345/771 |
| 6,714,925 | B1 | 3/2004 | Barnhill et al. | 706/48 |
| 6,731,781 | B1 | 5/2004 | Shams et al. | 382/129 |
| 6,760,715 | B1 | 7/2004 | Barnhill et al. | 706/16 |
| 6,789,069 | B1 | 9/2004 | Barnhill et al. | 706/12 |
| 6,839,454 | B1 | 1/2005 | Park | 382/128 |
| 6,990,221 | B2 | 1/2006 | Shams | 382/129 |
| 2002/0052882 | A1 | 5/2002 | Taylor | 707/104.1 |
| 2003/0100995 | A1 | 5/2003 | Loraine et al. | 702/19 |
| 2003/0148295 | A1 | 8/2003 | Wan et al. | 435/6 |
| 2004/0213446 | A1 | 10/2004 | Shams et al. | 382/129 |

OTHER PUBLICATIONS

BIO002—M. Taine and A. Herment, "Extraction of Heart and Vessel Walls on Ultrasound Images Using Snake-Splines", *SPIE*, vol. 2434, Mar. 1995, pp. 808-816.

BIO003—M. Jolly, S. Lakshmanan and A. Jain, "Vehicle Segmentation and Classification Using Deformable Templates", *IEEE*, vol. 18, No. 3, Mar. 1996, pp. 293-305.

BIO004—Y. Amit and A. Kong, "Graphical Templates for Model Registration", *IEEE*, vol. 18, No. 3, Mar. 1996, pp. 225-236.

BIO005—B. Olstad and A. Torp, "Encoding of a Priori Information in Active Contour Models", *IEEE*, vol. 18, No. 9, Sep. 1996, pp. 863-872.

BIO006—A. Abrantes and J. Marques, "A Class of Constrained Clustering Algorithms for Object Boundary Extraction", *IEEE*, vol. 5, No. 11, Nov. 1996, pp. 1507-1521.

BIO007—A. Jain Y. Zhong and S. Lakshmanan, "Object Matching Using Deformable Templates", *IEEE*, Vol. 18, No. 3, Mar. 1996, pp. 267-278.

BIO008—M. Kass, A. Witkin and D. Terzopoulos, "Snakes: Active Contour Models", *International Journal of Computer Vision*, 1998, pp. 321-331.

BIO009—S. Shams, "Multiple Elastic Modules for Visual Pattern Recognition", *Neural Networks*, vol. 8, No. 9, 1995, pp. 1439-1453.

BIO010—D. Shu, J. Nash, M. Eshaghian and K. Kim, "Straight-Line Detection on a Gated-Connection VLSI Network", *P IEEE Comp. Soc.*, Jun. 1990, pp. 456-461.

BIO011—S. Shams, "Translation-, Rotation, Scale-, and Distortion-Invariant Object Recognition Through Self-Organization", *International Journal of Neural Systems*, vol. 8, No. 2, Apr. 1997, pp. 173-179.

BIO012—Yidong Chen et al., "Ratio-Based Decisions and the Quantitative Analysis of cDNA Microarray Images", *Journal of Biomedical Optics*, vol. 2, No. 4, Oct. 1997, pp. 364-374.

BIO013—M. S. Boguski and G. D. Schuler, "Establishing a Human Transcript Map", *Nature Genetics*, vol. 10, No. 4, 1995, pp. 369-371.

BIO014—G. D. Schuler, M. S. Boguski, et al., "A Gene Map of the Human Genome", *Science*, Vol. 274, Issue 5287, Oct. 25, 1996, pp. 540-546.

Granjeaud et al., "From Hybridization Image to Numerical Values: A Practical, High Throughput Quantification System for High Density Filter Hybridizations", *Genetic Analysis: Biomolecular Engineering*, vol. 12, 1996, pp. 151-162.

Non-Final Office Action mailed Aug. 22, 2005, in U.S. Appl. No. 10/761,938. 20 pages.

APPARATUS, METHOD, AND COMPUTER PROGRAM PRODUCT FOR DETERMINING CONFIDENCE MEASURES AND COMBINED CONFIDENCE MEASURES FOR ASSESSING THE QUALITY OF MICROARRAYS

BACKGROUND (1) Technical Field

The present invention relates to image processing of biomaterial information, and more particularly to tools for processing the information contained in microarrays.

(2) Discussion

The bioinformatics field, which, in a broad sense, includes any use of computers in solving information problems in the life sciences, and more particularly, the creation and use of extensive electronic databases on genomes, proteomes, etc., is currently in a stage of rapid growth. In particular, much of the analysis of proteomic and genomic information is performed through the use of microarrays. Microarrays provide a means for simultaneously performing thousands of experiments, with multiple microarray tests resulting in many millions of data samples.

DNA is a primary example of the substances that are analyzed through the use of microarrays. However, many different types of biological chemicals such as proteins for example can also be analyzed using this technique. DNA microarray analysis has become an important source of information for geneticists, permitting the simultaneous monitoring of thousands of genes. As mentioned, modern microarrays contain tens of thousands of genes spotted on them. Once such a large volume of information is extracted from a microarray image, a wide variety of statistical techniques may be applied to make various decisions regarding the gene characteristics.

The data mining procedure typically performed on a microarray slide includes two main steps: image analysis and statistical data processing. As any statistical processing procedure may be influenced by the quality of its input, the statistical data processing step relies heavily on the image analysis step. The image analysis step typically comprises three stages: grid finding and spot location adjustment; spot region segmentation; and measurement extraction.

Grid finding is performed to locate the periodic grids of (usually circular) spots printed on a slide. The approximate grid structure is usually known in advance, and grid finding may be performed by a variety of well-known and effective searching procedures. Each image typically contains several subgrids that are also placed periodically with respect to each other. Deviations of subgrids and of individual spots (data points) from their expected positions on the slide can occur due to technical imperfections of the printing process. Spot location and size adjustment techniques are used to compensate for such deviations.

After each spot is locked on the image, the region around its center is ideally segmented into signal pixels, background pixels and ignored pixels. There are several techniques by which images may be segmented. The techniques vary from purely spatial to purely intensity based. Spatial schemes usually simply place a circular mask for the signal at its center location, assigning a "signal" label to every pixel within the circle. Intensity based schemes are based on analysis of the intensity distribution around the spot location, attempting to extract the signal distribution from the snip.

After the segmentation procedure is complete, the mean expression of the signal and the background may be measured along with their variances and other spatial and distributional quantities. To assess the quality of these measurements, a variety of approaches may be found in the literature, several of which are listed below for further reference. Generally, the source of low measured expression quality is rooted in the aforementioned three stages of the image analysis step, as well as to measurement contamination and misprints on the slide.

As mentioned, there are currently several general approaches to expression quality measurement. Two principally different groups of methods may be found in the literature: replicate-based quality assessment and image-based quality assessment. With regard to replicate-based quality assessment, spot replicates are considered to be a valuable source of information for example for significance analysis of differently expressed genes among other uses. However, before performing any kind of analysis, it is useful to analyze the distribution of replicate expressions and to remove the outliers, which usually appear due to defects in printing, scanning, or measurement extraction procedures. Techniques of varying complexity are currently available. However, the main drawback of this type of quality assessment is a necessity for a relatively large number of replicates. In order to generate somewhat flawless replicate measurements, a complicated design of experiments would be required to prevent the appearance of slide defects common for all replicates of an individual gene (sample).

On the other hand, with regard to confidence measures assessed through a direct image-based quality assessment, different quality measures may be used, with the choice depending mainly on the microarray design, the equipment sophistication, and the measurement extraction procedures. The most widely used set of measures includes the ratio of the signal standard deviation within the spot to its mean expression; the offset of a spot from its expected position in the grid; and measures of spot circularity (e.g. the ratio of squared perimeter to spot area).

These measures are taken independently, and are used in an independent manner from one another or are combined using basic logical operations, such as AND, OR, etc. Although these quality measures and their uses are of help in making decisions regarding the spot, currently, these values are not kept within specific bounds, which prevents them from being able to be used together in a synergistic manner. It is therefore desirable to provide a set of quality measurements that are bounded to a predetermined value range in order to permit their compatibility. It is further desirable to provide a system that uses a wider variety of quality measures, and it is more preferable that the system combines the various measures into an overall confidence measure for the data. By doing so, not only would a broader set of measures provide a more complete quality assessment, but combining the set of measures in a meaningful way would provide a more robust and flexible way of handling the issue of spot quality.

(1) Mei-Ling Ting Lee, F. C. Kuo, G. A. Whitmore, Jeffrey Sklar, "Importance of replication in microarray gene expression studies: Statistical methods and evidence from repetitive cDNA hybridizations", Proceedings of the National Academy of Science, August 2000, vol. 97, no. 18.

(2) Yidong Chen, E. R. Dougherty, M. L. Bittner, "Ratio-based decisions and the quantitative analysis of cDNA microarray images", Journal of biomedical optics, October 1997, no. 2(4).

(3) Yee Hwa Yang, M. J. Buckley, Sandrine Dudoit, T. P. Speed "Comparison of methods for image analysis on cDNA microarray data", Technical report #584, 2000, Department of Statistics, University of California, Berkeley.

(4) R. Adams, L. Bischof, "Seeded region growing", IEEE Transactions on Pattern Analysis and Machine Intelligence, 1994, no. 16.

(5) I. H. Witten, E. Frank, "Data Mining. Practical machine learing tools and techniques with Java implementations", Morgan Kaufmann publishers, 2000.

SUMMARY

An apparatus is provided for determining a confidence measure for the output of a process for assessing proteomic and genomic information samples. The output is represented as a set of measurements. The system comprises a memory for storing digital data generated from at least a portion of the measurements in the set of measurements and a processor coupled with the memory for accessing the digital data therefrom, and for determining a confidence measure for each of at least a portion of the signals for which digital data is stored in the memory. The confidence measure is indicative of a confidence level in the quality of the output of the process for assessing biochemical data.

The set of signals typically represent the ouptut of a process for assessing a set of proteomic and genomic data samples, which are then arranged as data points in a pre-determined spatial arrangement such that each data point has an expected position in a pre-determined spatial arrangement. The pre-determined spatial arrangement is preferably a grid-type array, and more specifically a multi-level grid. The pre-determined spatial arrangement is usually called a microarray.

In another embodiment, the confidence measure is a position offset confidence measure for the data point determined from the offest between the expected position of a data point and a respective actual position of the data point.

In still another embodiment, the confidence measure is a background contamination confidence measure for the data point determined by measuring the background contamination in an image snip surrounding a data point.

In yet another embodiment, the confidence measure is a signal contamination confidence measure for the data point determined by measuring the signal contamination.

In still another embodiment, each data point is represented by at least one pixel, with the pixels of the data point representing a subset of the pixels contained in an image snip, and where the confidence measure is an ignored pixel percentage confidence measure for the data point determined based on the percentage of the pixels in the snip representing the data point.

In a further embodiment, each data point has a perimeter, wherein each data point is contained in an image snip having borders, and wherein the confidence measure is an open perimeter confidence measure for the data point, determined based on the percentage of the perimeter of a data point occupied by the border of its respective snip.

In a still further embodiment, each data point has an expected shape and an actual shape, and where a shape regularity confidence measure for the data point is determined based on a comparison of the actual shape with the expected shape.

In a preferred embodiment, the processor is operative for determining at least two confidence measures and for combining confidence measures.

In a further preferred embodiment, the confidence measures are combined into combined confidence measure. The confidence measure includes at least one confidence measure selected from a group consisting of a normalized position offset confidence measure, a normalized background contamination confidence measure, a normalized signal contamination confidence measure, a normalized ignored pixel percentage confidence measure, a normalized open perimeter confidence measure, and a normalized shape regularity confidence measure. The normalization of each of the confidence measure includes a weighting factor to determine the relative contribution of each confidence measure to the combined confidence measure.

In a still further embodiment, the confidence measures are combined heuristically into a plurality of not-necessarily exclusive subsets, each including subset members, with each subset producing a subset confidence measure by heuristically weighting the subset members.

In a still further embodiment, each subset confidence measure for a particular data point is bounded at a predetermined bound level. When the subset confidence measure for a particular subset for the particular data point reaches the predetermined threshold level, a flag is produced for that data point, and wherein all flags produced for a particular data point are combined into a logical decision schema in order to determine whether to flag the data point.

In yet further embodiment, the confidence measures are combined using a machine-learning algorithm selected from a group consisting of supervised and unsupervised machine-learning algorithms to produce a combined confidence measure. The supervised machine-learning algorithm may be trained using a training set created by manually flagging data points considered to be defective. The machine-learning algorithm may be trained using a training set of flagged and not flagged data points created by means of a replicate-based outlier detection schema.

Each of the operations of the apparatus discussed above typically corresponds to a software module for performing the function on a computer. In other embodiments, the means or modules may be incorporated onto a computer readable medium to provide a computer program product. Also, the means discussed above also correspond to steps in a method for developing quality measures for proteomic and genomic data.

BRIEF DESCRIPTION OF THE DRAWINGS

The objects, features and advantages of the present invention will be apparent from the following detailed descriptions of the preferred embodiment of the invention in conjunction with reference to the following drawings where.

DETAILED DESCRIPTION

Figure 1:
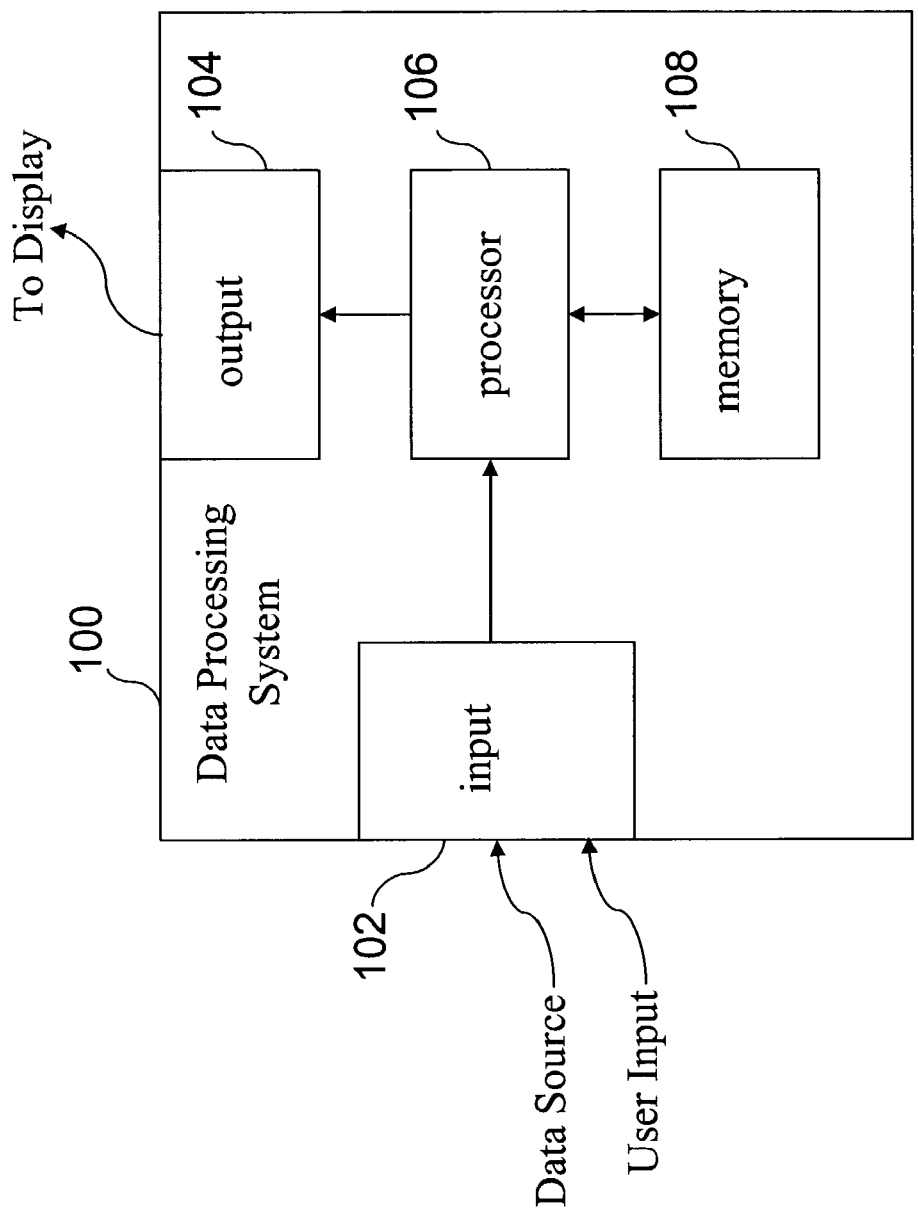
FIG. 1 is a block diagram depicting the components of a computer system used in the present invention.

The present invention relates to image processing of microarrays, and more particularly to tools for processing the information contained in a microarray. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In order to provide a working frame of reference, first a glossary of some of the terms used in the description and claims is given as a central resource for the reader. The glossary is intended to provide the reader with a "feel" for various terms as they are used in this disclosure, but is not intended to limit the scope of these terms. Rather, the scope of the terms is intended to be construed with reference to this disclosure as a whole and with respect to the claims below. Then, a brief introduction is provided in the form of a narrative description of the present invention to give a conceptual understanding prior to developing the specific details.

(1) Glossary

Before describing the specific details of the present invention, it is useful to provide a centralized location for various terms used herein and in the claims. The terms defined are as follows:

Means—The term "means" as used with respect to this invention generally indicates a set of operations to be performed on a computer. Non-limiting examples of "means" include computer program code (source or object code) and "hard-coded" electronics. The "means" may be stored in the memory of a computer or on a computer readable medium.

Bound(ed)—This term as used herein is intended to indicate a set of values between which a quality measure is permitted to range. Typically, the value is between 0.0 and 1.0. The actual mathematical or logical relationship for a particular quality measure need not be linear, and may be fitted to a curve as necessary for a particular embodiment. The measures may be bounded in the sense that a range over which a measure may vary is specified apriori so that all values which the measure may take fall within the range or are mapped onto the range.

(2) Introduction

The present invention provides a mechanism for assigning a confidence level regarding the quality of spots on a microarray. Several new confidence measures will be introduced for measuring the quality of image analysis output (i.e. assigning a confidence value to every measurement value received from a microarray), including a background contamination confidence measure; a signal contamination confidence measure; a position offset confidence measure; a percentage of ignored pixels confidence measure; a percentage of open perimeter confidence measure, and a shape regularity measure. Additionally, techniques for fusing the measures into an overall confidence measure are provided, including heuristic and machine-learning approaches. Note that analysis of microarray data is considered a separate issue and is not addressed herein, as the present invention may be used independent of any further statistical expression-related analysis.

(3) Physical Embodiments of the Present Invention

The present invention has three principal "physical" embodiments. The first is an apparatus for analyzing proteomic and genomic information obtained through the image processing of microarray assay results, typically in the form of a computer system operating software of in the form of a "hard-coded" instruction set. The second physical embodiment is a method, typically in the form of software, operated using a data processing system (computer). The third principal physical embodiment is a computer program product. The computer program product generally represents computer readable code stored on a computer readable medium such as an optical storage device, e.g., a compact disc (CD) or digital versatile disc (DVD), or a magnetic storage device such as a floppy disk or magnetic tape. Other, non-limiting examples of computer readable media include hard disks and flash-type memories. These embodiments will be described in more detail below.

A block diagram depicting the components of a computer system used in the present invention is provided in FIG. 1. The data processing system 100 comprises an input 102 for receiving image-based data, regarding proteomic and genomic information from a microarray, from a data source. Note that the input 102 may include multiple "ports" for receiving data and user input. Typically, user input is received from traditional input/output devices such as a mouse, trackball, keyboard, light pen, etc., but may also be received from other means such as voice or gesture recognition for example. The output 104 is connected with the processor for providing output. Output to a user is preferably provided on a video display such as a computer screen, but may also be provided via printers or other means. Output may also be provided to other devices or other programs for use therein. The input 102 and the output 104 are both coupled with a processor 106, which may be a general-purpose computer processor or a specialized processor designed specifically for use with the present invention. The processor 106 is coupled with a memory 108 to permit storage of data and software to be manipulated by commands to the processor.

Figure 2:
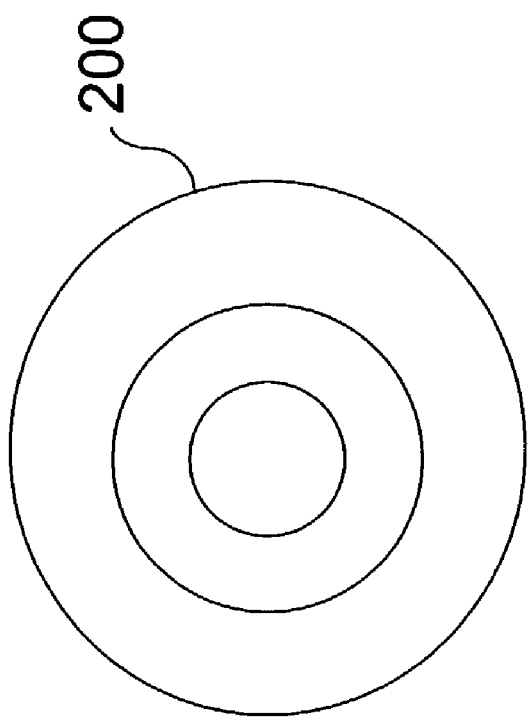
FIG. 2 is an illustrative diagram of a computer program product embodying the present invention.

An illustrative diagram of a computer program product embodying the present invention is depicted in FIG. 2. The computer program product 200 is depicted as an optical disk such as a CD or DVD. However, as mentioned previously, the computer program product generally represents computer readable code stored on any compatible computer readable medium.

(4) The Preferred Embodiments

In this discussion, first a set of quality measures used for assigning confidence levels to every spot on a microarray image are presented. The quality measures presented herein are intentionally bounded between a high value and a low value for normalization in order to facilitate their combination into a combined quality measure. After discussing the quality measures, techniques for combining them into a combined quality measure are discussed, including both heuristic techniques and machine-learning techniques.

(a) Quality Measures

The present invention is designed to assign a confidence level to every spot on a microarray image. In many cases, the intensity of the spots represent a set of gene or protein expression values, and the quality level of this expression measurement should be analyzed before proceeding with any kind of further data processing, in order to ensure the integrity of the experimental results. The use of such quality estimates may vary from simple exception of low-confidence expressions from further consideration (spot flagging) to utilizing of the confidence numbers in the data analysis stage (clustering, experiment significance analysis etc).

Sources of spot expression miscalculation can be separated into two general groups. The first group consists of measurement errors as consequences of defects introduced during the slide printing process. The other group consists of expression miscalculations resulting from poor performance of the spot finding and image segmentation techniques when applied to the image. Details regarding each of the quality measures are provided below, and they can be combined in order to account for sources of both spot expression miscalculation types.

i. Background Contamination Confidence Measure

A microarray image typically consists of one or several rectangular subgrids. The approximate structure of each subgrid, as well as the spacing between the subgrids is usually known, and is characterized by the type of printing and scanning hardware used for the particular experiment. Background defects may appear in arbitrary parts of an image for various reasons, and may influence the intensity level of all spots located in the contaminated area. It is assumed that the output of the segmentation procedure for each spot region includes spot pixels and background pixels around the spot, and that ignored pixels also may exist. The ignored pixels are usually isolated from the rest of the image to avoid local contaminations (such as those caused by dust particles) from influencing the measurement. In determining the background contamination confidence measure, the mean of the background intensity around the spot is taken as the local background estimate. In an ideal situation, when no contamination occurs across the image, according to the Central Limit Theorem, the background means will be approximately normally distributed. There are two scenarios that are worthy of consideration: where the image contains multiple subgrids and where the image contains only one subgrid.

In the case where there are multiple subgrids, to assess the parameters for the distribution of the background means, first the least contaminated subgrid is detected. In order to do so, the means across every subgrid are averaged, with the results denoted by $\mu_i$, i=1, ..., N, where N represents the number of subgrids in the image. The subgrid delivering the median of the average means for the series of subgrids $\mu_j$, is taken as the least contaminated subgrid and is used as a basis for computing the distribution parameters for local background means. Taking the median serves as a filtering process for excluding contaminated subgrids. On the selected subgrid (the median subgrid), the average value of the background means $\mu_{med,ave}$ and their standard deviation $\sigma_{med,ave}$ are computed. The current spot's background mean is denoted here by x. The argument of the standard normal cumulative distribution function is equal to $$y = \frac{|x - \mu_{med,ave}|}{\sigma_{med,ave}}$$

in the following equation:

$$p_y = \frac{1}{\sqrt{2\pi}} \int_{-\infty}^{y} \exp\left(-\frac{t^2}{2}\right) dt.$$

This value will range from 0.5 to 1.0 for every spot. $Q=2(1-p_y)$ is used as a quality measure for the background level of the current spot with Q being the background contamination quality measure. The further the background mean is from $\mu_{med,ave}$, the lower the quality number is. To flag a spot for low background quality, the background contamination quality measure Q may be flagged at some low level threshold $Q_0$. Thus, the measure is thresholded in order to set a point value at which a flag is issued. The value of threshold $Q_0$ is chosen according to acceptable level of false alarm, in other words number of "healthy" spots flagged out due to random deviations $$N_{fa} = \frac{M}{Q_0},$$

where M is the total number of spots on the image.

Next, the situation will be considered where only one subgrid is on the image. To assess parameters $\mu$, $\sigma$ we take the background means of spots within the subgrid, excluding the region of m×n spots around the current spot, where n and m are chosen such that m×n represents the expected size of contamination. Note that the number of values used for computing the statistics $\mu$, $\sigma$ should be not less than 30 to assure necessary accuracy of the estimates. All the rules for spot flagging and quality number evaluation are completely analogous to those in the case with multiple subgrids, with the only difference that the pair $\mu$, $\sigma$ may be different for every spot.

Figure 3:
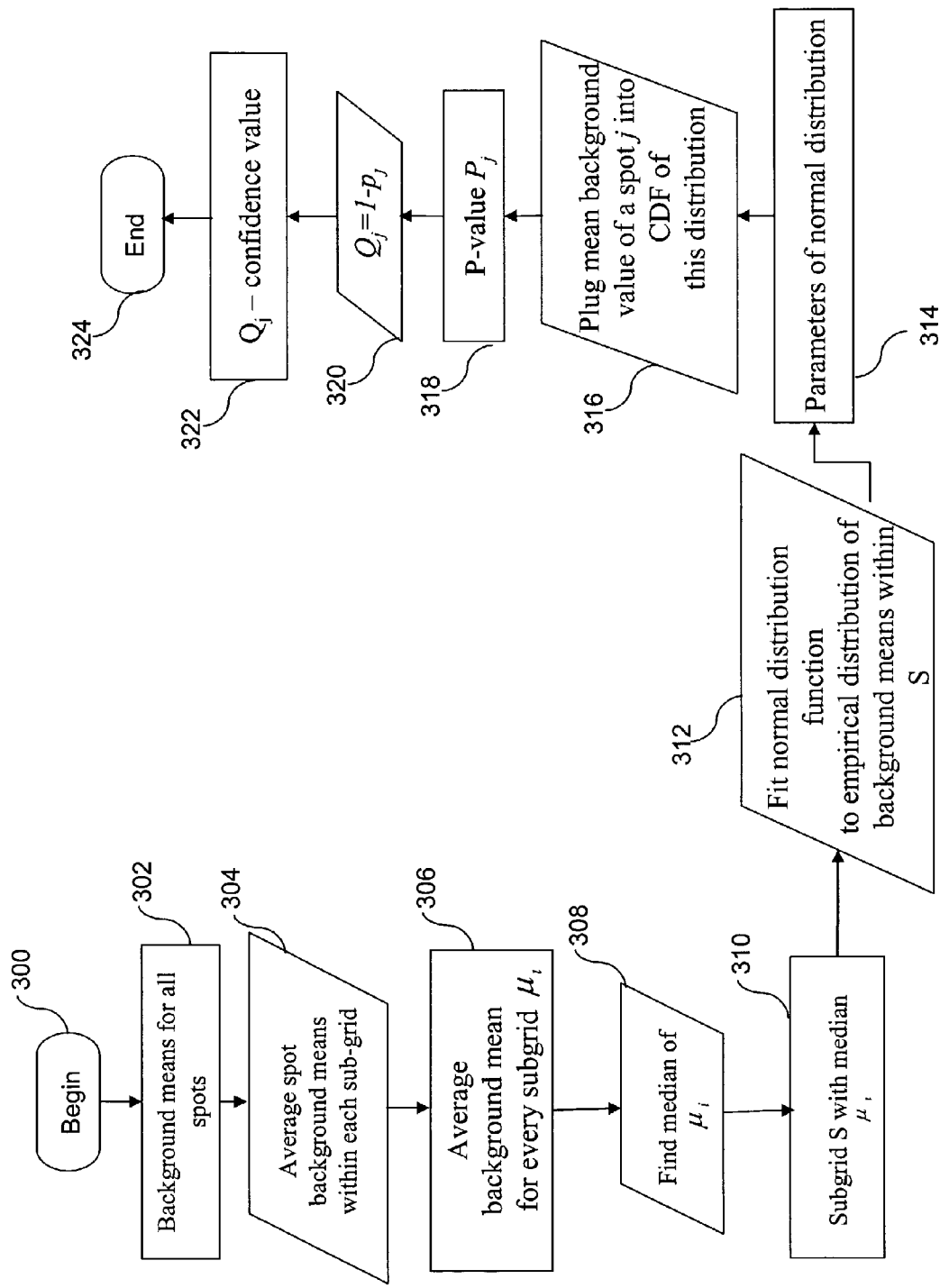
FIG. 3 is a flow diagram of the preferred process for generating the background contamination confidence measure.

The process for generating the background contamination measure just described is generally illustrated in FIG. 3. After beginning 300, the background means for all spots on the slide are calculated 302. Next, the spot background means within each subgrid are averaged 304 in order to generate an average background mean for every subgrid 306. The median of the average background means for every subgrid is then determined 308, and the subgrid S that is at the median is determined 310. A normal distribution function is then fitted to the empirical distribution of background means within the subgrid S 312. As a result, the parameters of the normal distribution are derived 314. The mean background value of a spot is then put into the cumulative distribution function of this distribution 316, and a value p for the equation defined above is generated 318, which allows for the use of the equation $Q_j=1-p_j$ 320 to determine the confidence value $Q_j$ 322 at the end 324 of the procedure.

Figure 4:
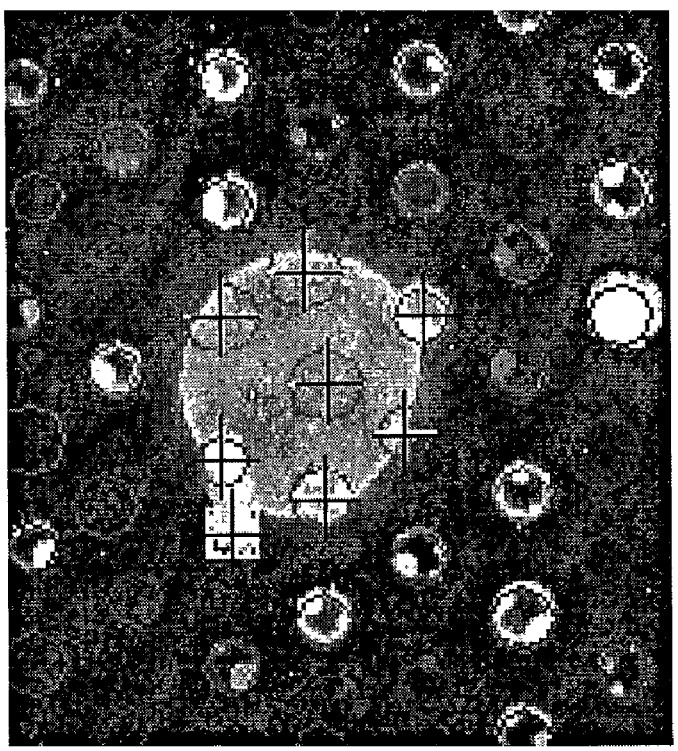
FIG. 4 is an image depicting the result of the generation of the background confidence measure, wherein the flagging results are shown.

An image of a subgrid of 12×32 spots each is shown in FIG. 4. The image was processed using a microarray image processing software package (such as Imagene 4.2 by Biodiscovery, Inc. of Marina Del Rey, Calif.). The spots with quality values lower than 0.95 are marked with a "+". Varying levels may be provided for confidence values as well, such as the use of coloring or grayscale levels to indicate varying degrees of confidence. The 0.95 value in this case may be used as a simple flag to indicate a spot having an overly low confidence value.

ii. Signal Contamination Confidence Measure

Another possible source of signal disturbance is misplacement of material on the slide. To assess this quality, the signal volatility within a spot is analyzed. High volatility generally results in lower confidence in the measured value. Spot intensity variance may be used as an estimate of signal volatility. The spot variance distribution can also be approximated by using a normal distribution function. However, experience has shown that the parameters of such a probability strongly depend on the mean intensity level of the spot. Thus, to retrieve the information about signal variance distribution all of the spots on the image are grouped by their intensity levels. The spots are then sorted by mean intensity $\overline{X}_j$ in order to split them into the bins with equal numbers of spots. The number of bins is preferably chosen to be either 100 or $$\frac{M}{30},$$

whichever is the smaller. If the number of bins becomes less than 5, analysis can not be accurately performed. However, with the modern microarray technology allowing for more than 1000 spots per grid, this is rarely a case of concern. Next, the standard deviation of intensity level for each spot $$S_j = \frac{1}{G_j - 1} \sum_{l=1}^{G_j} (X_j^l - \overline{X}_j)^2$$

is computed for each spot j, where $G_j$ represents the number of pixels belonging to the spot region and $X_j^l$ represents the measured intensity of each respective pixel. Next, the bin k to which the current spot belongs is determined. The sample mean $\mu_k$ and sample standard deviation $\sigma_k$ of the spot intensity standard deviations $S_j$ within each bin are then calculated, excluding the current spot from the measurements. For the current spot, the standard normal cumulative distribution functions is evaluated with the argument $$\frac{S_j - \mu_k}{\sigma_k}.$$

The resulting value, $p_y$, will range from 0.0 to 1.0. As with the background contamination confidence measure, Q=1−p will be used as a quality measure for the signal stability of the current spot. To flag the spot for low quality, the measure Q can be thresholded at some low level $Q_0$. The value of the threshold level $Q_0$ is chosen according to acceptable level of false "alarm", in other words the number of "healthy" spots flagged out due to random deviations $$N_{fa} = \frac{M}{Q_0},$$

where M is the total number of spots on the image.

Figure 5:
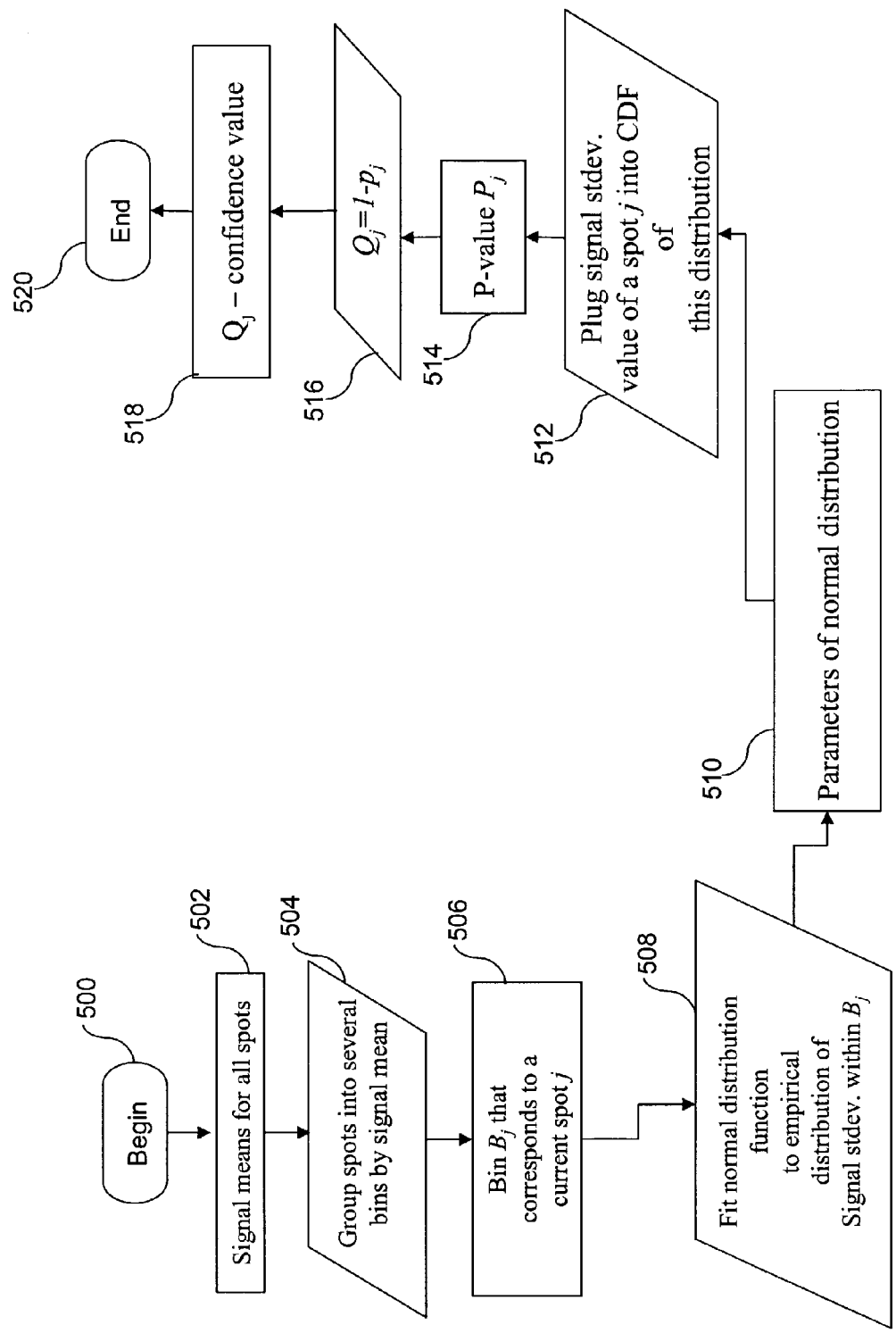
FIG. 5 is a flow diagram of the preferred process for generating the signal contamination confidence measure.

The general procedure for determining a signal contamination confidence measure is shown in FIG. 5. After beginning 500, the signal means for all spots are determined 502, and the spots are then grouped into a set of bins based on the value of their signal means 504. For a bin corresponding to a current spot 506, a normal distribution is fitted to the empirical distribution of the signal standard deviation within that bin 508. The parameters of the normal distribution for the bin are then generated 510. The signal standard deviation value of a spot is then put into the cumulative distribution function of this distribution 512, and a value p for the equation defined above is generated 514, which allows for the use of the equation $Q_j=1-p_j$ 516 to determine the confidence value $Q_j$ 518 at the end 520 of the procedure.

Figure 6:
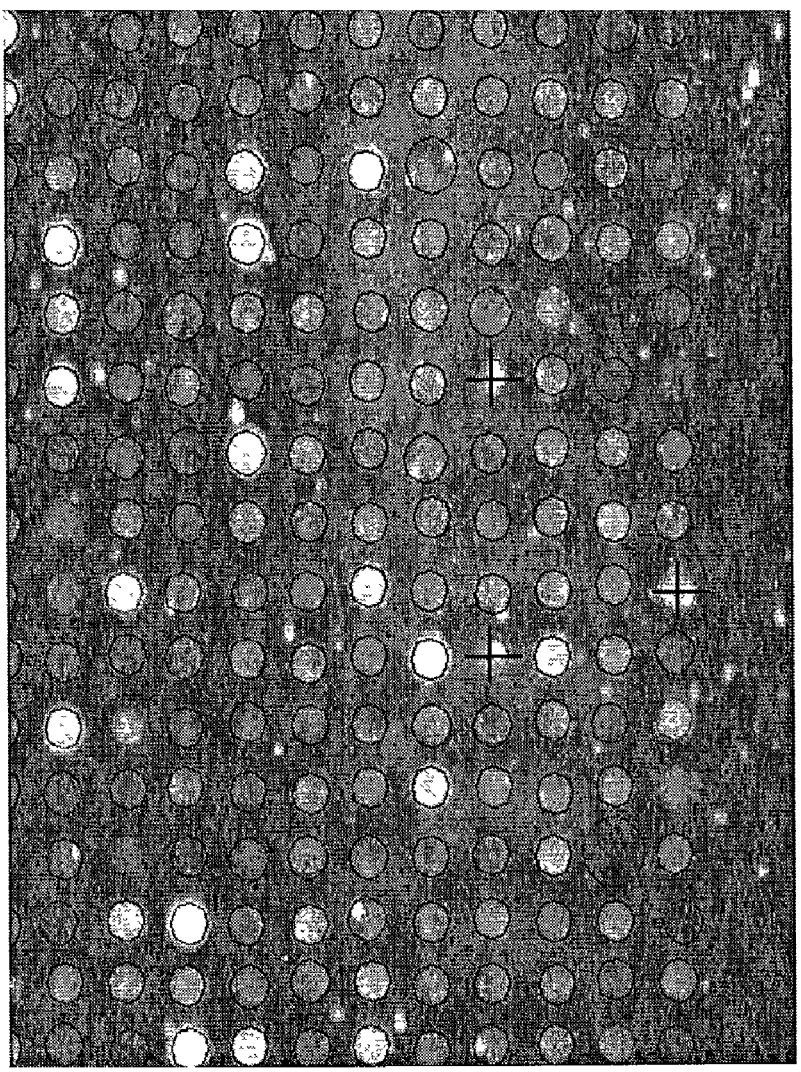
FIG. 6 is an image depicting the result of the generation of the signal contamination confidence measure, wherein the flagging results are shown.

FIG. 6 is an image depicting the result of the generation of the signal contamination confidence measure, wherein the flagging results are shown by spots marked with a "+". This picture is analogous to FIG. 4. The spots marked (flagged) by the "+"s are those having quality values below 0.95. As discussed before, various coloring or brightness schemes may be used to indicate varying levels of confidence. Another issue when using this confidence number is the type of measurement estimate used for the spot. If the spot intensity median or mode were chosen for an estimate of measurement (such as gene expression measurement), such estimation procedure appears to be quite stable with respect to volatility of the signal and threshold could be set slightly higher without increasing the false alarm rate.

iii. Position Offset Confidence Measure

A combination of spot finding and image segmentation procedures yields an estimate for each spot's center location (i.e., the mass center of spot region). However, the expected position of each spot may also be calculated according to microarray grid structure (for example, by using a least-squares fit on a strictly rectangular grid). In ideal conditions with no significant deviations of the spots from their expected positions, it is expected that the coordinate shifts of the spots are approximately normal in both vertical and horizontal directions. Thus, letting $x_j$ and $y_j$ be the spot center deviations from the expected position in horizontal and vertical directions, respectively. A pool of 2M such deviations is constructed, with one deviation per coordinate per spot. The sample variance is computed from the respective pool for each spot, with the pool for each spot constructed by removing current spot from the overall pool. The result is denoted by $$S_{\textit{off}_j}^2.$$

For every spot, the cumulative distribution function of Rayleigh distribution is computed using the parameter and an argument equal to $$r_j = \sqrt{x_j^2 + y_j^2}.$$

The form of the distribution is:

$$p_{r_j} = \int_0^{r_j} \frac{t}{S_{off_j}^2} \exp\left(-\frac{t^2}{2S_{off_j}^2}\right) dt.$$

The $P_{r_j}$ will range from 0.0 to 1.0. Again, the quality measure $Q=1-P_{r_j}$ will be used as a metric for the precision of the spot's location relative to the other spot positions. As with the other quality measures, a spot may be flagged for low signal quality by thresholding Q at some low level, $Q_0$. The value of threshold $Q_0$ is chosen according to the acceptable level of "false alarm". As before, this is defined as the number of good quality spots flagged out due to random deviations $$N_{fa} = \frac{M}{Q_0},$$

where M represents the total number of spots on the image.

Figure 7:
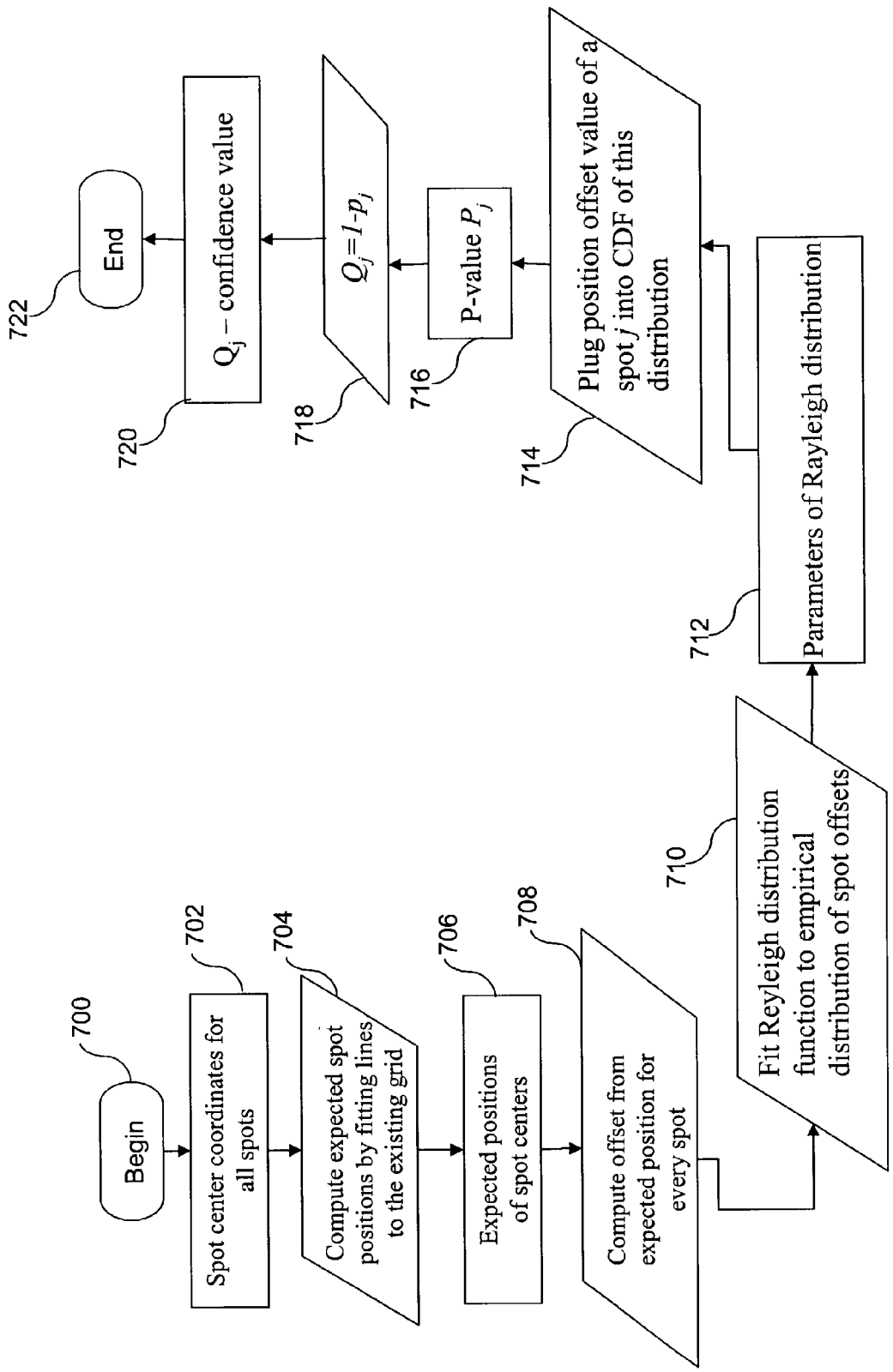
FIG. 7 is a flow diagram of the preferred process for generating the position offset confidence measure.

A flow diagram of the general process for generating the position offset confidence measure is shown in FIG. 7. After beginning 700, the spot center coordinates for all of the spots in the area of interest are determined 702. The expected spot positions are then computed 704, yielding the expected positions of the spot centers 706. Next, for every spot, its offset from its expected position is computed 708. A distribution function, preferably a Reyleigh distribution function, is then fitted to the empirical distribution of the spot offsets 710, and the parameters of the Rayleigh distribution are thus determined 712. The position offset value of a spot is then put into the cumulative distribution function 714. This yields a value p for the equation defined above 716, which, in turn, allows for the use of the equation $Q_j=1-p_j$ 718 to determine the confidence value $Q_j$ 720 at the end 722 of the procedure.

Figure 8:
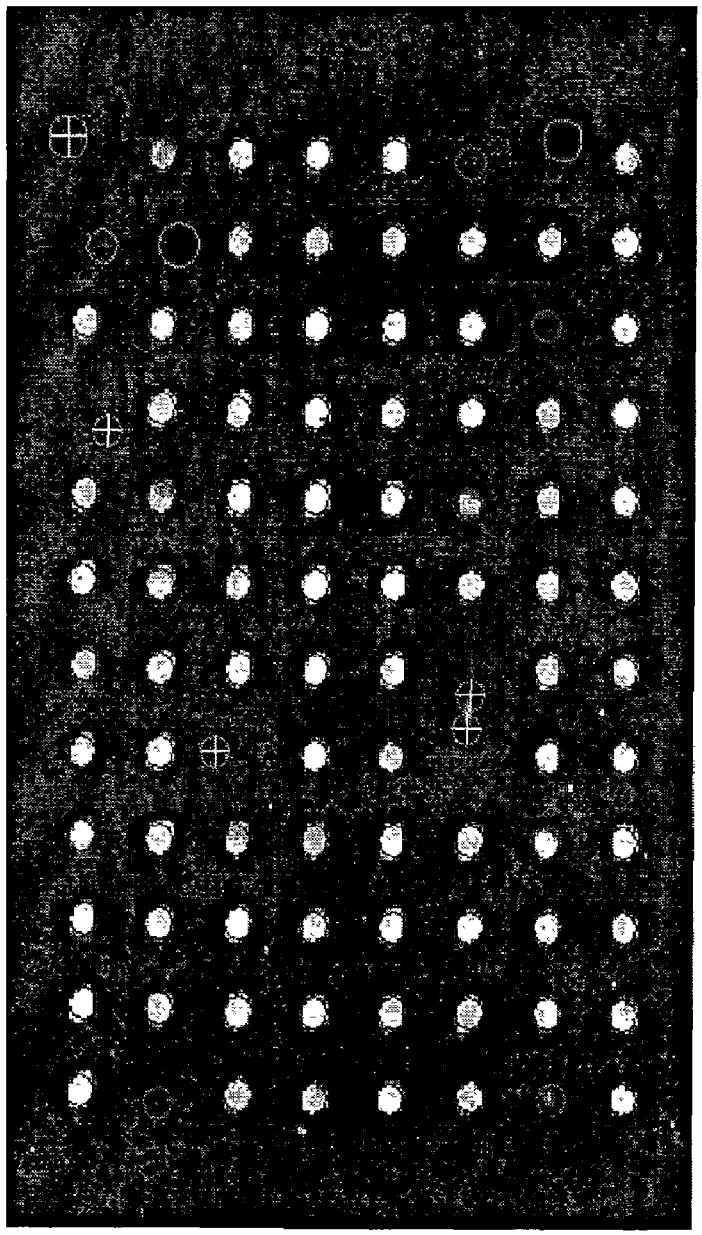
FIG. 8 is an image depicting the result of the generation of the position offset confidence measure, wherein the flagging results are shown.

FIG. 8 is an image depicting the result of the generation of the position offset confidence measure, wherein the flagging results are shown by spots marked with a "+". This picture is analogous those shown in FIG. 4 and 6. The spots marked (flagged) by the "+"s are those having quality values below 0.95. As discussed before, various coloring or brightness schemes may be used to indicate varying levels of confidence. Flagged spots are considered too far from their expected position to be able to be associated with that position, and are thus considered irrelevant.

iv. Percentage of Ignored Pixels Confidence Measure

The signal contamination confidence measure does not include any information regarding how many pixels were ignored during the segmentation procedure. Such information provides additional help in assessing spot quality. In order to determine the percentage of ignored pixels confidence measure, first the total number of pixels in the ignored regions directly neighboring the signal region is computed for every spot. Next, for each spot, the ratio $$R_j = \frac{\text{\# of ignored pixels neighboring the signal}}{\text{\# of signal pixels} + \text{\# of ignored pixels neighboring the signal}} \times 100\%$$

is computed. For different microarrays, different values of this ratio may be acceptable. Thus the threshold for flagging the spot may be set at some level $R_0$. All spots with a ratio higher than the threshold are flagged. In general practice, it has been found that a ratio, $R_j$, below 10% is acceptable.

Figure 9:
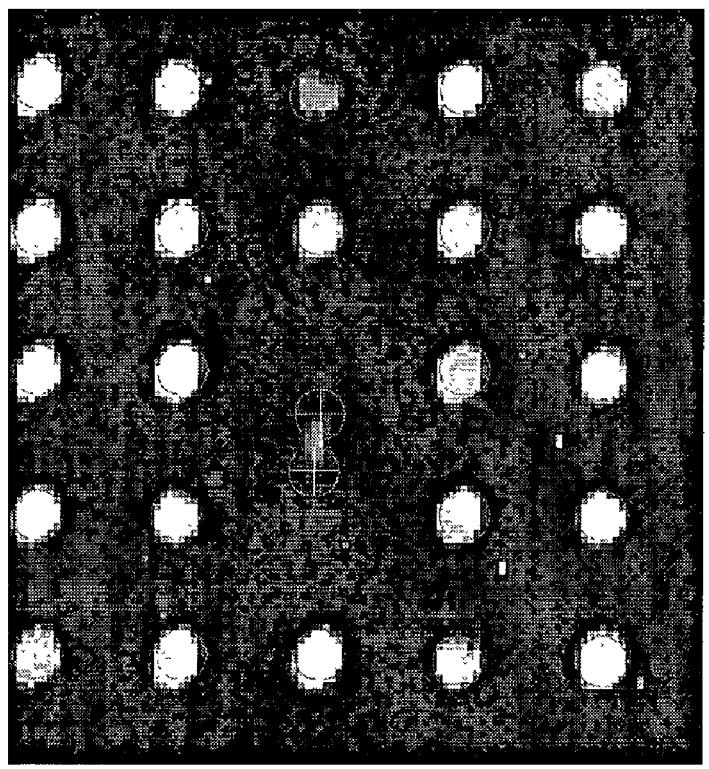
FIG. 9 is an image depicting the result of the generation of the percentage of ignored pixels confidence measure, wherein the flagging results are shown.

FIG. 9 is an image depicting the result of the generation of the percentage of ignored pixels confidence measure, wherein the flagging results are shown. The threshold level was set at 10% for the figure for illustrative purposes only. In practice, the threshold is preferably selected according to the microarray design type. For example, for donut-shaped spots, the middle part will always be ignored resulting in a need to increase the threshold by roughly 20%-40%. The threshold also should be chosen according to the researcher's tolerance to number of contaminated pixels. If the researcher decides that 50% of the spot area is enough for reliable estimate, than the threshold should be adjusted accordingly.

v. Percentage of Open Perimeter Confidence Measure

Sometimes the segmentation procedure isolates a wrong region as measured signal. Usually this is the case when there is a narrow contamination extended onto the territory of several spots. Position offset and background contamination procedures cannot always determine such cases (especially in the cases such as where a spot is not visible or where a narrow contamination extends across the spot's bounding area). In these cases the perimeter of spot signal, $P_{total}$, may be computed along with the length of the open perimeter $P_{open}$—that part of signal boundary that coincides with the spot's region bounding box (the box around the spot, in which the segmentation procedure was performed). The ratio $$\tilde{R} = \frac{P_{open}}{P_{total}} \times 100\%$$

is used as a measure of the percentage of "open" perimeter of the spot signal, e.g. percentage of open perimeter confidence measure. The thresholding for flagging in for this measure is performed by setting the value, $R_0$, at some predetermined level. Next, all of the spots having ratios higher than the threshold are flagged. As a rule of thumb, it has been found that a value for $R_j$ of below 5% is acceptable. Again, however, this threshold is preferably subject to adjustment according to current experimental conditions. Sometimes because of high spatial density of spots on the slide, open perimeters occur systematically.

vi. Shape Regularity Confidence Measure

This measure characterizes closeness of spot's border to a circular shape. The first step of this algorithm is to inscribe a signal area of a spot into a circle. Next, the number of non-signal pixels that fall within the circle is computed and divided by circle's area. This ratio is subtracted from 1 and is termed "shape regularity". This variable ranges from 0.0 (highly non-circular shape) to 1.0 (a perfect circle). Note however, that there may be cases where a shape other than a circle is desired. In these cases, this confidence measure can be adjusted accordingly to account for other shapes. Whenever this ratio falls below the predetermined threshold for a spot, the spot can be flagged as a spot of low quality.

(c) Further Discussion Regarding the Confidence Measures

The aforementioned confidence measures can be divided into two groups: probabilistic (the first three) and absolute (the last three). The advantage of probabilistic approach is that it is adoptive to any particular microarray structure and image intensity level with no additional tuning requirement. Another advantage is that, in order to create a combined confidence measure, all three quantities may simply be summed with equal weights with the result retaining its probabilistic meaningfulness (assuming that the sum of the weights is equal to 1.0). Although the three probabilistic confidence measures and the three absolute confidence measures may be used either individually or in groups, their use as a combined whole is highly preferred. If the measures are used as a simple combination, a spot is flagged as of low quality whenever at least one of the tools produces a flag.

All six aforementioned metrics are responsible for different aspects of spot contamination. Simply introducing a logical "OR" for flagging based on these metrics is sufficient for most contamination types. Such a logic statement would produce a flag whenever at least one of six measures exceeds the pre-set threshold.

The number of confidence values used can be reduced if it is likely that a specific type of contamination will never appear in particular experimental conditions or if it is considered insignificant.

The statistical nature of the first three measures is essential for detecting the targeted defects. If the statistical approach discussed above is not used, the thresholds for the absolute measurements such as the background mean and the signal standard deviation would need to be adjusted manually for every new image because of possible changes in overall intensities. However, the global approach presented above will provide an auto adjustment of first three metrics based on the overall level of corresponding measurements throughout the image.

The scheme presented herein is intended to provide a reliable scheme for detecting defects. Experiments have yielded a performance that can be superior to the manual flagging made by a human operator. This effect comes from ability of aforementioned statistics to detect slight abnormalities in spot measurements. Taking into the account further sophisticated statistical analysis that is usually performed on the data, elimination of such abnormalities may be of a significant value.

(d) Machine Learning

As discussed above, the confidence measures can be used along with a set threshold value to flag every measurement as a potentially low quality measurement.

A system constructed to use the confidence measures described above requires threshold values as an input in order to establish a single flag. A simple, heuristic approach to setting up the thresholds was mentioned above. However, it is preferred that a supervised or unsupervised learning technique, such as a decision tree, neural network, or a set of classification rules, be used for selecting the threshold values. In order to utilize this method, it is necessary to provide a significant number of images with predetermined quality flags for training.

The means for organizing the machine learning approach depends, to some degree, on the researcher's goals. If, for example, a researcher is only interested in reproducing a particular set of rules for spot flagging used by human operators, the choice of training data is obvious. A representative set of images with manually flagged spots should be provided.

However, a different technique is also provided, which relies on an objective knowledge of the possible distribution of the spot's expression. The concept of this method is based on elimination of outlier spots within the replicate distribution. If a sufficient number of replicates are available, an outlier detection procedure can be used to flag out unusual replicate expressions for every gene. The most naïve approach would be fitting a normal distribution and tagging any replicate outside a $3\hat{\sigma}$ distance (for example) from the average as an outlier. In this case $\hat{\sigma}$ is an estimate of a standard deviation for the normal distribution. Results of flagging procedure are then provided to a learning schema to produce appropriate thresholds for objective measures described in the previous section. There are currently several machine-learning techniques available for this purpose. After the training is complete, there will not be any need for the replicates, and the spot quality flagging system will be able to function autonomously utilizing the received thresholds. Generally, when the type of array changes the training stage must be repeated. This approach will not only provide an objective way to choose the thresholds, but will also provide flagging specific for any particular type of microarray image.

Taking one step further, a machine-learning approach can be used to combine all of the employed quality metrics into a single combined confidence (quality) measure, which characterizes the confidence in spot's expression, and which can be propagated into various statistical analysis tools.

In order to employ a machine-learning technique for combining various confidence measures into a single overall confidence value, it is necessary to use a training set which contains examples of various measurements along with their corresponding confidence values plus the desired overall confidence number. Since we do not have a priori knowledge of what a measurement overall confidence value should be, we have devised a method to estimate this using replicate spot measurements. The procedure is as follows. First a set of representative spot measruments are made along with the calculation of various measurement confidence values. Then, a procedure, such as the one described earlier, is used to combine these replicates (possibly removing outliers) to arraive at a single measurement for the spot. Any type of replicate combination can be used here. For example, the mean or median value of all replicates can be used. The mean or median values can be selected over all replicates or after the removal of outliers. Since these spots are all suppose to have the same value, the assumption here is that the combined value is a good representation of the true measurements for the spot. In the next step we can compare the measurement value of each spot against the combined replicate. This is especially true for those spots that were removed as outliers in case this scheme was used in replicate combination. We can use the difference between the actaull measurement value of the spot from the estimated true spot measure (the combined value) as an indication of the confidence value that can be associated with the measurement. Any number of methods can be used to compare the actaull measurement from the estimated true value such a s simple subtraction. This difference value now provide us a measure of confidence in the spot measurement. In the next step this value can be used as the desired output of a learning system which is given as input a set of spot measurement confidence values, and potentially, the actual spot measurements as well. In one embodiment a multi-layer neural network can be used to implement this supervided learning method. It is conceivable to use any number of other learning approaches, such as Selforganizing Maps, Nearest neighbor classifiers, decision trees, fuzzy K-means, and so forth to accomplish this objective. FIG. 11 shows a multi-layer perceptron network used to accomplish the learning.

Figure 10:
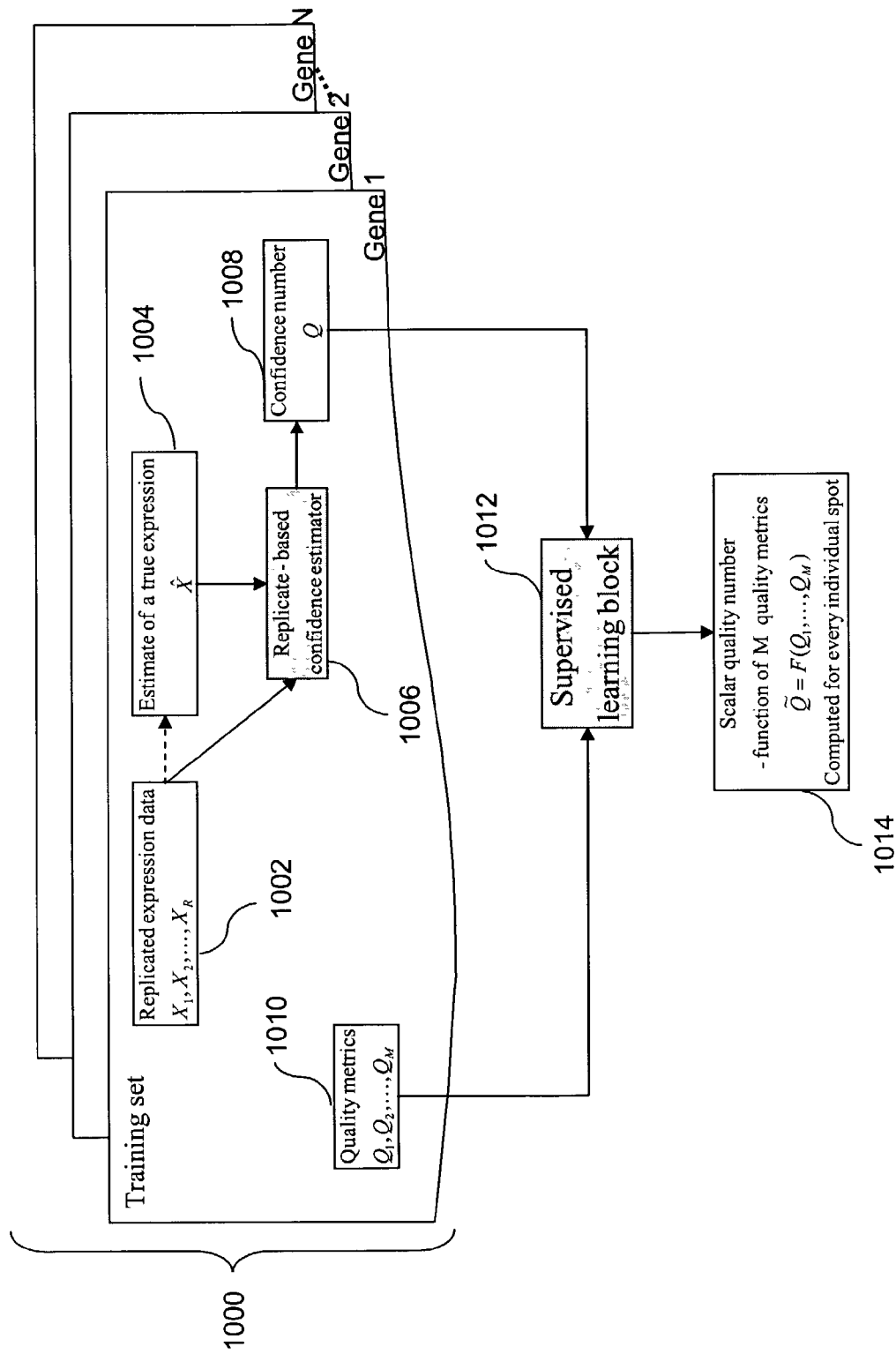
FIG. 10 is a block diagram illustrating the approximate data flow schema for training based on replicate-wise confidence levels.

Once the learning algorithem is used to establish a mapping between various spot measurment confidence values and a single overall confidence value, the system can be used in a "feed forward" or non-learning mode and simply used to predict the overall spot confidence based on the individual measurement confidence values. A number of different models can be learned for different types of slides or images and the correct model can be selected by the user or automaticaly during system operation. The block diagram depicted in FIG. 10 illustrates an approximate data flow schema for training based on replicate-wise confidence levels. The training set 1000 includes a set of genes, for which replicated expression data 1002 is used to generate an estimate of the true expressions to occur 1004. The replicate expression data 1002 and the estimate 1004 are used to create a replicate-based confidence estimator 1006, which generates confidence numbers Q 1008. The confidence number, along with quality metrics 1010 are provided to a supervised learning block 1012, which then generates a scalar quality number from a function of the quality metrics, for each individual spot 1014. Again, a variety of different, and well-known, machine-learning techniques may be employed for combining a set of existing quality characteristics into a single quality value based on the training set. As a result, after the training stage has been performed, a scalar quality number can be provided for every new spot based on the set the spot's quality metrics.

Both machine-learning schemas just discussed can be implemented based on aforementioned set of six quality metrics (or a subset thereof) as well as any other set of quality metrics desired.

What is claimed is:

1. A computer-implemented apparatus for determining a bounded confidence measure for an output of a process for assessing proteomic or genomic data samples, with the output represented as a set of signals, the apparatus comprising:
   (a) a memory that receives and stores digital data from a data source, wherein the digital data is generated from at least a portion of the signals in the set of signals; and
   (b) a processor coupled with the memory that accesses the digital data from the memory, and that determines a bounded confidence measure for each of at least a portion of the signals for which digital data is stored in the memory;
   wherein the bounded confidence measure is indicative of a confidence level in the quality of the output of the process for assessing proteomic or genomic data samples, and wherein the bounded confidence measure ranges between a predetermined set of values,
   the set of signals arranged as data points, with each data point having a perimeter, and each data point contained in an image snip having borders, the bounded confidence measure being an open perimeter bounded confidence measure for the data point, determined based on a percentage of the perimeter of a data point occupied by the border of the respective snip of the data point, the image snip comprising the data point and pixels in a bordered region surrounding the data point, and the bounded confidence measure stored in the memory.

2. A computer-implemented apparatus for determining a bounded confidence measure for an output of a process for assessing proteomic or genomic data samples, with the output represented as a set of signals, the apparatus comprising:
   (a) a memory that receives and stores digital data from a data source, wherein the digital data is generated from at least a portion of the signals in the set of signals; and
   (b) a processor coupled with the memory that accesses the digital data from the memory, and that determines a bounded confidence measure for each of at least a portion of the signals for which digital data is stored in the memory; wherein the bounded confidence measure is indicative of a confidence level in the quality of the output of the process for assessing proteomic or genomic data samples, and wherein the bounded confidence measure ranges between a predetermined set of values, the processor operative to determine at least two bounded confidence measures and to combine the at least two bounded confidence measures, the at least two bounded confidence measures combined heuristically into a plurality of subsets, each including subset members, with each subset having associated with it a subset bounded confidence measure produced by heuristically weighting the subset members, and a single bounded confidence measure which can be included in more than one subset, and the bounded confidence measure stored in the memory; and the set of signals arranged as data points, each subset bounded confidence measure for a particular data point bounded at a predetermined threshold level, and when the subset bounded confidence measure for a particular subset for the particular data point reaches the predetermined threshold level, a flag is produced for each data point in the subset, and all flags produced for a particular data point are combined into a logical decision schema in order to determine whether to flag the data point.

3. The computer-implemented apparatus of claim 2, the subset bounded confidence measure including at least one bounded confidence measure selected from a group consisting of a normalized position offset bounded confidence measure, a normalized background contamination bounded confidence measure, a normalized signal contamination bounded confidence measure, a normalized open perimeter bounded confidence measure, and a normalized shape regularity bounded confidence measure, and normalization of each of the at least two bounded confidence measures include a weighting factor to determine the relative contribution of each of the at least two bounded confidence measures to the subset bounded confidence measure.

4. The computer-implemented apparatus of claim 2, the subset bounded confidence measures including at least one bounded confidence measure selected from a group consisting of a normalized position offset bounded confidence measure, a normalized background contamination bounded confidence measure, a normalized signal contamination bounded confidence measure, a normalized open perimeter bounded confidence measure, and a normalized shape regularity bounded confidence measure, and normalization of each of the at least two bounded confidence measures include a weighting factor to determine the relative contribution of each of the at least two bounded confidence measures to the subset bounded confidence measure.

5. A computer-implemented apparatus for determining a bounded confidence measure for an output of a process for assessing proteomic or genomic data samples, with the output represented as a set of signals, the apparatus comprising:
   (a) a memory that receives and stores digital data from a data source, wherein the digital data is generated from at least a portion of the signals in the set of signals; and
   (b) a processor coupled with the memory that accesses the digital data from the memory, and that determines a bounded confidence measure for each of at least a portion of the signals for which digital data is stored in the memory;
   wherein the bounded confidence measure is indicative of a confidence level in the quality of the output of the process for assessing proteomic or genomic data samples, and wherein the bounded confidence measure ranges between a predetermined set of values,
   the processor operative to determine at least two bounded confidence measures and to combine the at least two bounded confidence measures, the at least two bounded confidence measures combined using a machine-learning algorithm selected from a group consisting of supervised and unsupervised machine-learning algorithms to produce a combined bounded confidence measure, and the machine learning algorithm trained using a training set of flagged data points created by means of a replicate-based outlier detection schema, and the bounded confidence measure is stored in the memory.

6. The computer-implemented apparatus of claim 5, the combined bounded confidence measure including at least one bounded confidence measure selected from a group consisting of a normalized position offset bounded confidence measure, a normalized background contamination bounded confidence measure, a normalized signal contamination bounded confidence measure, a normalized open perimeter bounded confidence measure, and a normalized shape regularity bounded confidence measure, and normalization of each of the at least two bounded confidence measures include a weighting factor to determine the relative contribution of each of the at least two bounded confidence measures to the combined bounded confidence measure.

7. A computer-implemented method for determining a bounded confidence measure for an output of a process for assessing proteomic or genomic data samples, with the output represented as a set of signals, the method comprising:
   (a) receiving digital data from a data source, wherein the digital data is generated from at least a portion of the signals in the set of signals;
   (b) determining a bounded confidence measure for each of at least a portion of the signals;
   wherein the bounded confidence measure is indicative of a confidence level in a quality of the output of the process for assessing proteomic or genomic data samples, and wherein the bounded confidence measure ranges between a predetermined set of values; and
   (c) storing the bounded confidence measure in a memory, the set of signals arranged as data points, with each data point having a perimeter, and each data point contained in an image snip having borders, the bounded confidence measure being an open perimeter bounded confidence measure for the data point, determined based on a percentage of the perimeter of a data point occupied by the border of the respective snip of the data point, the image snip comprising the data point and pixels in a bordered region surrounding the data point.

8. A computer-implemented method for determining a bounded confidence measure for an output of a process for assessing proteomic or genomic data samples, with the output represented as a set of signals, the method comprising:
   (a) receiving digital data from a data source, wherein the digital data is generated from at least a portion of the signals in the set of signals;
   (b) determining a bounded confidence measure for each of at least a portion of the signals; wherein the bounded confidence measure is indicative of a confidence level in a quality of the output of the process for assessing proteomic or genomic data samples, and wherein the bounded confidence measure ranges between a predetermined set of values; and
   (c) storing the bounded confidence measure in a memory, and determining a bounded confidence measure further comprising the determination of at least two bounded confidence measures combining the at least two bounded confidence measures, the at least two bounded confidence measures combined heuristically into a plurality of subsets, each including subset members, with each subset producing a subset bounded confidence measure by heuristically weighting the subset members, and a single bounded subset confidence measure can be included in more than one subset; wherein the set of signals arranged as data points, and each subset bounded confidence measure for a particular data point bounded at a predetermined threshold level, and when the subset bounded confidence measure for a particular subset for the particular data point reaches the predetermined threshold level, a flag is produced for each data point in the subset, and all flags produced for a particular data point are combined into a logical decision schema in order to determine whether to flag the data point.

9. The computer-implemented method of claim 8, the subset bounded confidence measure including at least one bounded confidence measure selected from a group consisting of a normalized position offset bounded confidence measure, a normalized background contamination bounded confidence measure, a normalized signal contamination bounded confidence measure, a normalized open perimeter bounded confidence measure, and a normalized shape regularity bounded confidence measure, and normalization of each of the at least two bounded confidence measures include a weighting factor to determine the relative contribution of each of the at least two bounded confidence measures to the subset bounded confidence measure.

10. The computer-implemented method of claim 8, the subset bounded confidence measures including at least one bounded confidence measure selected from a group consisting of a normalized position offset bounded confidence measure, a normalized background contamination bounded confidence measure, a normalized signal contamination bounded confidence measure, a normalized open perimeter bounded confidence measure, and a normalized shape regularity bounded confidence measure, and normalization of each of the at least two bounded confidence measures include a weighting factor to determine the relative contribution of each of the at least two bounded confidence measures to the subset bounded confidence measure.

11. A computer-implemented method for determining a bounded confidence measure for an output of a process for assessing proteomic or genomic data samples, with the output represented as a set of signals, the method comprising:
   (a) receiving digital data from a data source, wherein the digital data is generated from at least a portion of the signals in the set of signals;
   (b) determining a bounded confidence measure for each of at least a portion of the signals; wherein the bounded confidence measure is indicative of a confidence level in a quality of the output of the process for assessing proteomic or genomic data samples, and wherein the bounded confidence measure ranges between a predetermined set of values; and
   (c) storing the bounded confidence measure in a memory, and determining a bounded confidence measure further comprising determining at least two bounded confidence measures and combining the at least two bounded confidence measures, the at least two bounded confidence measures combined using a machine-learning algorithm selected from a group consisting of supervised and unsupervised machine-learning algorithms to produce a combined bounded confidence measure, and the machine learning algorithm trained using a training set of flagged data points created by means of a replicate-based outlier detection schema.

12. The computer-implemented method of claim 11, the combined bounded confidence measure including at least one bounded confidence measure selected from a group consisting of a normalized position offset bounded confidence measure, a normalized background contamination bounded confidence measure, a normalized signal contamination bounded confidence measure, a normalized open perimeter bounded confidence measure, and a normalized shape regularity bounded confidence measure, and normalization of each of the at least two bounded confidence measures include a weighting factor to determine the relative contribution of each of the at least two bounded confidence measures to the combined bounded confidence measure.

13. A computer readable medium storing a computer program for execution by at least one processor, the computer program for determining a bounded confidence measure for an output of a process for assessing proteomic or genomic data samples, with the output represented as a set of signals, the computer program comprising sets of instructions for:
   (a) receiving digital data from a data source, wherein the digital data is generated from at least a portion of the signals in the set of signals;
   (b) determining a bounded confidence measure for each of at least a portion of the signals; wherein the bounded confidence measure is indicative of a confidence level in the quality of the output of the process for assessing proteomic or genomic data samples, and wherein the bounded confidence measure ranges between a predetermined set of values; and
   (c) storing the bounded confidence measure in a memory, the set of signals arranged as data points, with each data point having a perimeter, and each data point contained in an image snip having borders, the bounded confidence measure being an open perimeter bounded confidence measure for the data point, determined based on a percentage of the perimeter of a data point occupied by the border of the respective snip of the data point, the image snip comprising the data point and pixels in a bordered region surrounding the data point.

14. A computer readable medium storing a computer program for execution by at least one processor, the computer program for determining a bounded confidence measure for an output of a process for assessing proteomic or genomic data samples, with the output represented as a set of signals, the computer program comprising sets of instructions for:
   (a) receiving digital data from a data source, wherein the digital data is generated from at least a portion of the signals in the set of signals;
   (b) determining a bounded confidence measure for each of at least a portion of the signals; wherein the bounded confidence measure is indicative of a confidence level in the quality of the output of the process for assessing proteomic or genomic data samples, and wherein the bounded confidence measure ranges between a predetermined set of values; and
   (c) storing the bounded confidence measure in a memory, the set of instructions for determining a bounded confidence measure further comprising the determination of at least two bounded confidence measures and combining the at least two bounded confidence measures, the at least two bounded confidence measures combined heuristically into a plurality of subsets, each including subset members, with each subset producing a subset bounded confidence measure by heuristically weighting the subset members, and a single bounded subset confidence measure can be included in more than one subset; wherein the set of signals arranged as data points, and each subset bounded confidence measure for a particular data point is bounded at a predetermined threshold level, and when the subset bounded confidence measure for a particular subset for the particular data point reaches the predetermined threshold level, a flag is produced for each data point in the subset, and all flags produced for a particular data point are combined into a logical decision schema in order to determine whether to flag the data point.

15. The computer program product of claim 14, the subset bounded confidence measure including at least one bounded confidence measure selected from a group consisting of a normalized position off set bounded confidence measure, a normalized background contamination bounded confidence measure, a normalized signal contamination bounded confidence measure, a normalized open perimeter bounded confidence measure, and a normalized shape regularity bounded confidence measure, and normalization of each of the at least two bounded confidence measures include a weighting factor to determine the relative contribution of each of the at least two bounded confidence measures to the subset bounded confidence measure.

16. The computer program product of claim 14, the subset bounded confidence measures including at least one bounded confidence measure selected from a group consisting of a normalized position offset bounded confidence measure, a normalized background contamination bounded confidence measure, a normalized signal contamination bounded confidence measure, a normalized open perimeter bounded confidence measure, and a normalized shape regularity bounded confidence measure, and normalization of each of the at least two bounded confidence measures includes a weighting factor to determine the relative contribution of each of the at least two bounded confidence measures to the subset bounded confidence measure.

17. A computer readable medium storing a computer program for execution by at least one processor, the computer program product for determining a bounded confidence measure for an output of a process for assessing proteomic or genomic data samples, with the output represented as a set of signals, the computer program product usable with a computer system including a processor, a memory coupled with the processor, an input coupled with the processor for receiving the set of signals, the computer program product comprising means, stored on a computer readable medium, sets of instructions for:
  (a) receiving digital data from a data source, wherein the digital data is generated from at least a portion of the signals in the set of signals; and
  (b) determining a bounded confidence measure for each of at least a portion of the signals; wherein the bounded confidence measure is indicative of a confidence level in the quality of the output of the process for assessing proteomic or genomic data samples, and wherein the bounded confidence measure ranges between a predetermined set of values; and
  (c) storing the bounded confidence measure in a memory, the set of instructions for determining a bounded confidence measure further comprises determining at least two bounded confidence measures and combining the at least two bounded confidence measures, the at least two bounded confidence measures combined using a machine-learning algorithm selected from a group consisting of supervised and unsupervised machine-learning algorithms to produce a combined bounded confidence measure, and the machine learning algorithm trained using a training set of flagged data points created by means of a replicate-based outlier detection schema.

18. The computer program product of claim 17, the combined bounded confidence measure including at least one bounded confidence measure selected from a group consisting of a normalized position offset bounded confidence measure, a normalized background contamination bounded confidence measure, a normalized signal contamination bounded confidence measure, a normalized open perimeter bounded confidence measure, and a normalized shape regularity bounded confidence measure, and normalization of each of the at least two bounded confidence measures include a weighting factor to determine the relative contribution of each of the at least two bounded confidence measures to the combined bounded confidence measure.

* * * * *